United States Patent
Nakajima et al.

(10) Patent No.: US 6,538,019 B1
(45) Date of Patent: Mar. 25, 2003

(54) FUNCTIONAL EMULSIONS

(75) Inventors: Mitsutoshi Nakajima, Ibaraki (JP); Hiroshi Nabetani, Ibaraki (JP); Sosaku Ichikawa, Ibaraki (JP); Qing Yi Xu, Ibaraki (JP)

(73) Assignees: Japan as represented by Director of National Food Research Institute, Ministry of Agriculture, Forestry and Fisheries, Ibaraki (JP); Bio-Oriented Technology Research Advancement Institution, Tokyo (JP)

( * ) Notice: Subject to any disclaimer, the term of this patent is extended or adjusted under 35 U.S.C. 154(b) by 85 days.

(21) Appl. No.: 09/639,541

(22) Filed: Aug. 16, 2000

(30) Foreign Application Priority Data

Mar. 29, 2000 (JP) ........................................ 2000-090441

(51) Int. Cl.[7] ................................................ A01N 43/02
(52) U.S. Cl. ........................... 514/449; 516/20; 516/54; 426/601; 552/544
(58) Field of Search ..................... 516/20, 54; 514/449; 426/601; 552/544

(56) References Cited

U.S. PATENT DOCUMENTS

| | | | |
|---|---|---|---|
| 4,089,947 A | * | 5/1978 | Horii et al. |
| 5,407,683 A | * | 4/1995 | Shively |
| 5,587,149 A | * | 12/1996 | Punto et al. |
| 6,080,394 A | * | 6/2000 | Lin et al. |

FOREIGN PATENT DOCUMENTS

| | | | |
|---|---|---|---|
| FR | 09203585 | * | 3/1992 |
| FR | 2689011 A | * | 10/1993 |
| JP | 357068124 A | * | 4/1982 |
| JP | 57171431 A | * | 10/1982 |
| JP | 357171431 A | * | 10/1982 |
| JP | 59016813 A | * | 1/1984 |
| JP | 61015732 A | * | 1/1986 |
| JP | 61127786 A | * | 6/1986 |
| JP | 62216635 | * | 9/1987 |
| JP | 62225240 A2 | * | 10/1987 |
| JP | 409149765 A | * | 6/1997 |
| JP | WO-973078 A1 | * | 8/1997 |
| JP | 10327777 A | * | 12/1998 |
| JP | 411276881 A | * | 10/1999 |

OTHER PUBLICATIONS

Pandley, I.P., Study of the viscosities of complex alcohol/oil, Asian J. Chem, 4(4), 917–19, 1992.*

* cited by examiner

Primary Examiner—Paul J. Killos
(74) Attorney, Agent, or Firm—Carrier, Blackman & Associates, P.C.; Joseph P. Carrier; William D. Blackman

(57) ABSTRACT

According to the present invention, it is possible to produce emulsions containing a material that are insoluble or that have low solubility with respect to water and oil in a high concentration, so as to obtain emulsions which can be preserved for a long period of time. More specifically, ethanol, to which polyglycerol oleic acid ester (PG) is added, and vegetable oil, are stirred with a homogenizer or an emulsification method such as a membrane emulsification or a microchannel emulsification, thereby obtaining E/O type emulsions or E/O/W type emulsions wherein ethanol drops in which polyphenol is dissolved in a high concentration are dispersed into vegetable oil.

20 Claims, 2 Drawing Sheets

FUNCTIONAL EMULSIONS

BACKGROUND OF THE INVENTION

1. Field of the Invention

The present invention relates to functional emulsions for use in food, drugs and cosmetics, etc.

2. Description of Related Art

Many products are manufactured and sold in a state of emulsion to make the products easier to eat and use as well as to extend the preservation term of the products. As examples, margarine and ice cream can be listed as food, ointment as drugs, and cosmetic cream as cosmetics.

Almost all the conventional emulsions are an oil-in-water (O/W) type or a water-in-oil type (W/O) in which water is used as a continuous phase and oil is used as a dispersed phase, and a water-in-oil-in-water (W/O/W) type or an oil-in-water-in-oil (O/W/O) type which is a combined type. Emulsions according to the present invention have not been studied yet.

At present polyphenols, such as catechin or the like, attract much attention as antioxidants. Almost all polyphenols are insoluble or have low solubility with respect to water. Therefore, so far, when polyphenols were applied in foods, drugs or cosmetics, it was impossible to present it in an emulsified form, or if it was possible, such form could not be kept for a long period of time, because phase separation occurred in a short time. Also, it was impossible to introduce polyphenols into emulsions at a high concentration.

In addition to polyphenol, many functional components, such as androstenedione which is known as a steroid hormone, taxol which is an anticancerous terpenoid, validamycin which is known as an agent for controlling sheath blight, or the like, are generally low in solubility with respect to water and oil. Therefore, since it is difficult to produce a dispersion system which contains these components in a high concentration and they must be used in a extremely low concentration, the efficiency is low and the range of viable applications for them is limited.

SUMMARY OF THE INVENTION

The present invention takes into consideration that a method of using a material insoluble or of low solublility with respect to water or oil as an emulsion dispersion system has not yet been established. According to the present invention, there is provided functional emulsions wherein a material being insoluble or having low solubility with respect to water and oil is dissolved in alcohol and the alcohol is dispersed in oil as a dispersed phase.

There is also provided functional emulsions wherein a material being insoluble or having low solubility with respect to water and oil is dissolved in alcohol, the alcohol is dispersed in oil as a dispersed phase, and the oil is dispersed in water as a dispersed phase.

As materials that is insoluble or has low solubility with respect to water and oil, polyphenols such as catechin, anthocyanin, quercetin or the like can be listed as materials having a relation to foods. Catechin and anthocyanin are known as polyphenols which are slightly soluble in water. However, many polyphenols, such as quercetin or the like, almost never dissolve in water. Some slightly dissolve in vegetable oil. In contrast, however, these materials show high solubility of around 20–30% with respect to alcohol such as ethanol or the like. Therefore, according to the present invention, it is possible to establish a stable dispersion system of a high concentration by dispersing such alcohol into oil.

In addition, as a material that is insoluble or has low solubility with respect to water and oil, androstenedione which is known as steroid hormone, taxol which is an anticancerous terpenoid, or validamycin which is known as an agent for controlling sheath blight can be listed. However, other functional components may be listed.

Any emulsifying agent (surfactant) is required to obtain emulsions by dispersing alcohol into oil. It is preferable to use nonionic polyglycerol fatty acid ester as such emulsifying agent. In more detail, tetraglycerol monoester (MO310), hexaglycerol monoester (MO500) or polyglycerol oleic acid ester (MO750: HLB12.9) can be listed as other such emulsifying agents.

As oil comprising a continuous phase of emulsions, vegetable oil is preferable and, specifically, triglyceride can be listed as an example of such.

As an alcohol, methanol, hydrous methanol, ethanol, hydrous ethanol, propanol, hydrous propanol, butanol or hydrous butanol is used. It is preferable to make the ratio of oil with respect to alcohol at least 8:2 by volume. When the ratio of alcohol as a dispersed phase is increased to above the preferable ratio, unwanted phase separation occurs readily.

DESCRIPTION OF THE PREFERRED EMBODIMENTS

Hereinafter, detailed explanation of the embodiments according to the present invention will be given making reference to the attached drawings.

First, sunflower seed oil (having the triolein purity 90% or more, as produced by Nippon Lever B. V.) as a continuous phase, 95% ethanol as a dispersed phase, and polyglycerol oleic acid ester (MO750, HLB12.9) as an emulsifying agent (surfactant) were prepared.

Next, polyphenol was dissolved in ethanol. As the polyphenol to be used, catechin, anthocyanin, quercetin can be listed. In the following embodiment, catechin was used and the addition ratio was 20 wt % with respect to ethanol.

Thereafter, the ethanol, to which 1 wt % polyglycerol oleic acid ester (PG) was added, and triolein (sunflower seed oil) were stirred at 3000 rpm for ten minutes with a homogenizer (Polytron: PT3000), thereby attempting the production of an emulsion.

The means for producing emulsions is not limited to the homogenizer. It is also possible to use an emulsification method such as a membrane emulsification, a microchannel emulsification which is industrially advantageous, or the like.

Figure 1:
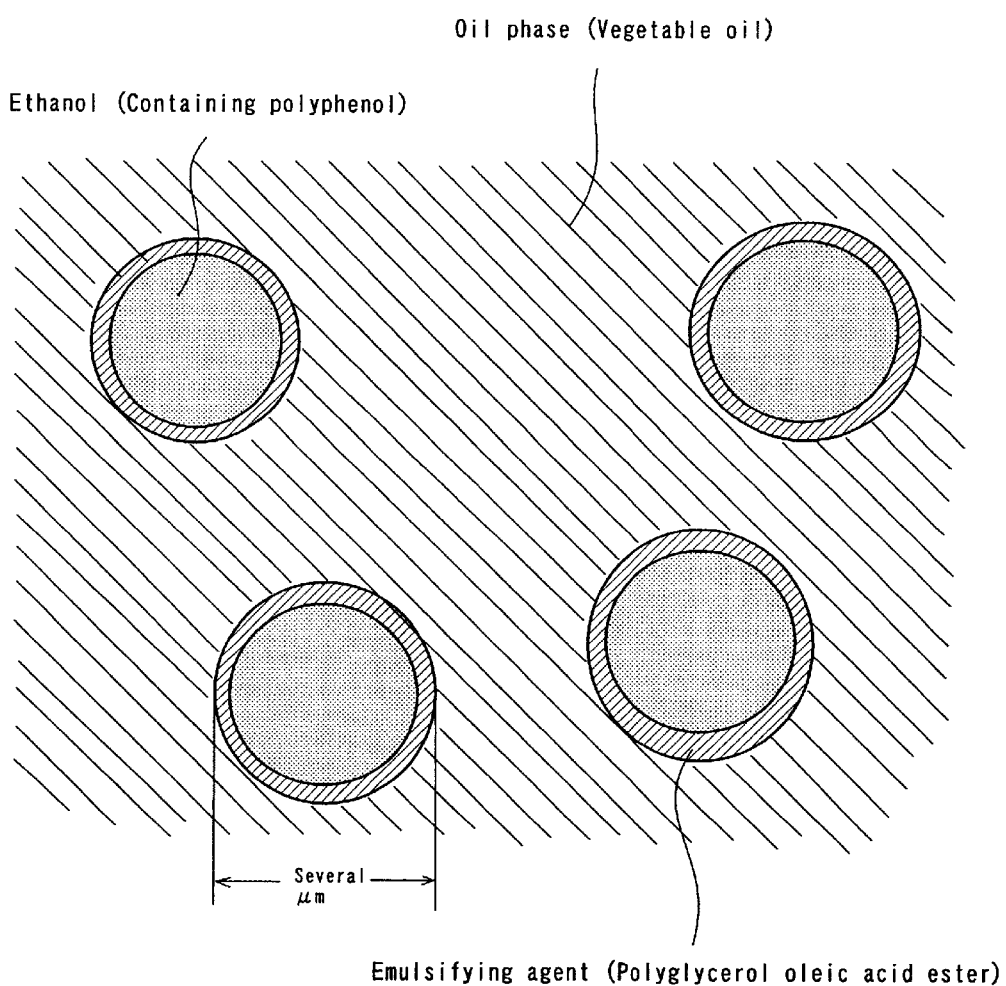
FIG. 1 is an enlarged conceptual view of a functional emulsion according to an aspect of the present invention.

As shown in FIG. 1, ethanol drops in which polyphenol is dissolved are dispersed in an oil phase (triolein), and polyglycerol oleic acid ester (PG) occupies the boundary surface between the ethanol drops and the oil phase. Herein, the particle diameter of the ethanol drop was measured with the Laser Diffraction Particle Distribution Analyzer (SALD-200ER, produced by Shimadzu Corp.) and it was found to be several $\mu$m.

Figure 2:
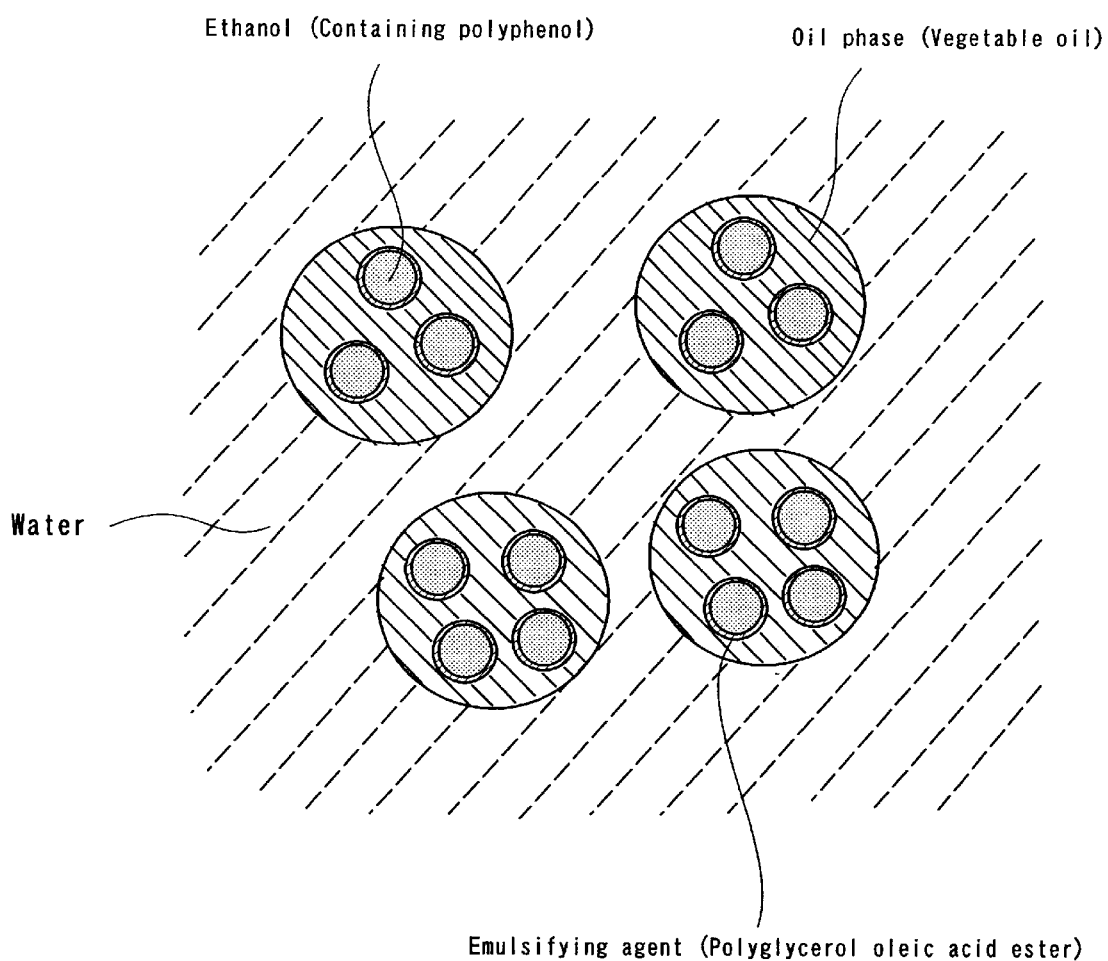
FIG. 2 is an enlarged conceptual view of a functional emulsion according to another aspect of the present invention.

The emulsion shown in FIG. 2 is an E/O/W type emulsion which was produced by using an E/O type emulsion, which was obtained as mentioned above, as a dispersed phase, and water as a continuous phase. Such emulsions having a triple phase system can be employed in a much wider range of applications.

The following Table 1 shows the relationship between the ratio of triolein and ethanol (to which PG is added) and the stability of the emulsion.

As is made apparent by results shown in Table 1, the samples in which the ratio of triolein and ethanol was 8:2 and 9:1 did not undergo phase separation until five months. However, the sample having the ratio of 6:4 reached phase separation within four days. When the ratio of ethanol was increased more than this, such samples underwent phase separation early and stability decreased.

TABLE 1

| Ratio of triolein and ethanol | Stability | Emulsification Type |
|---|---|---|
| 2:8 | − | E/O |
| 3:7 | − | E/O |
| 4:6 | − | E/O |
| 5:5 | + | E/O |
| 6:4 | ++ | E/O |
| 7:3 | ++ | E/O |
| 8:2 | +++ | E/O |
| 9:1 | +++ | E/O |

−: The sample reached perfect phase separation within one day.
+: The sample reached perfect phase separation within two days.
++: The sample reached perfect phase separation within four days.
+++: The sample did not reach phase separation until five months.
The concentration of the emulsifying agent: 1%

Next, the addition amount of polyglycerol oleic acid ester (PG) was variously changed within the range of 1 wt %–5 wt % and the stability of the emulsions was examined by a turbidity method. A conspicuous change in emulsion stability was not found.

Further, the dispersion behavior of the polyglycerol oleic acid ester (PG) was examined using a small-angle X-ray scattering method (SAXS). It turned out that the polyglycerol oleic acid ester (PG) in ethanol was a molecular assembly having the radius of inertia of about 7 Å and the polyglycerol oleic acid ester (PG) in triolein was a molecular assembly having the radius of inertia of about 90 Å. As a result, it can be said that the stability of emulsions can be achieved by increasing the ratio of triolein with respect to ethanol.

However, if the ratio of ethanol was decreased, the extent to which polyphenol can be taken into the emulsions was also decreased. Therefore, the ratio of triolein and ethanol is preferably 6:4 or more, and more preferably 8:2 to 9:1.

Furthermore, the possibility of using emulsifying agents other than polyglycerol oleic acid ester (PG) was examined. The results are shown in Table 2. In Table 2, DAO750 indicates decaglycerol decaester, PO500 indicates hexaglycerol pentaester, PO310 indicates tetraglycerol pentaester, MO310 indicates tetraglycerol monoester, MO500 indicates hexaglycerol monoester, and MO750 indicates polyglycerol oleic acid ester.

TABLE 2

| | | Emulsifying Agent | | | | | | | | | | | | |
|---|---|---|---|---|---|---|---|---|---|---|---|---|---|---|
| Emulsion Type | | Sorbitan ester | | | | Polyglycerol fatty acid ester | | | | | | Lecithin | | | |
| | Monoglyceride | Span 85 | Span 80 | Span 60 | Span 40 | DAO750 | PO500 | PO310 | MO310 | MO500 | MO750 | Soy (Wako) | Soy (Sigma) | Yolk (Wako) | Yolk (Sigma) |
| E/O | − | − | + | + | + | − | − | − | ++ | ++ | +++ | + | + | + | + |

−: The sample caused the perfect phase separation within one day.
+: The sample caused the perfect phase separation within two days.
++: The sample did not cause the perfect phase separation within four days.
+++: The sample did not cause the phase separation until five months.
The concentration of the emulsifying agent: 5%
The ratio of triolein and ethanol: 8:2
Wako and Sigma indicate the name of the manufacturer.

Table 2 shows that tetraglycerol monoester, hexaglycerol monoester and polyglycerol oleic acid ester (MO750) are preferable as an emulsifying agent from the group comprising polyglycerol fatty acid esters. In particular, polyglycerol oleic acid ester (MO750) is most preferable. In a case of using another emulsifying agent, phase separation can easily occur.

In the above-mentioned embodiment, polyphenol was used as a material being dissolved in alcohol. However, in the present invention, a material having higher solubility with respect to alcohol than with respect to water and oil can be widely used instead of polyphenol.

As is explained in the above, according to the present invention, it is possible to produce emulsions containing various materials in a high concentration, such as polyphenol, androstenedione, taxol or validamycin, or the like, which to date could not be made in the form of emulsions due to the insolubility or low solubility thereof with respect to water and oil.

As a result of this, it is possible to extend the preservation term of an emulsion containing polyphenol, androstenedione, taxol or validamycin and like materials being insoluble or having low solubility in water and oil, and increase the available applications, options and methods for the use of these materials.

Although there have been described in detail what are the present embodiments of the invention, it will be understood by persons skilled in the art that variations and modifications may be made thereto without departing from the gist, spirit or essence of the invention. The scope of the invention is indicated by the appended claims.

What is claimed is:

1. An emulsion for use in food, drugs and cosmetics, comprising alcohol as a dispersed phase dispersed into oil as a continuous phase with an emulsifying agent, and a material which is insoluble or having low solubility with respect to water and oil dissolved into said alcohol in a high concentration, and wherein a ratio of said oil with respect to said alcohol is at least 8:2.

2. An emulsion for use in food, drugs and cosmetics, comprising oil as a dispersed phase dispersed into water as a continuous phase, alcohol as a dispersed phase dispersed into said oil as a continuous phase with an emulsifying agent, and a material which is insoluble or having low solubility with respect to water and oil dissolved into said alcohol in a high concentration, and wherein a ratio of said oil with respect to said alcohol is at least 8:2.

3. An emulsion according to claim 1, wherein said material which is insoluble or having low solubility with respect to water and oil comprises polyphenol.

4. An emulsion according to claim 3, wherein said material which is insoluble or having low solubility with respect to water and oil comprises polyphenol, and said polyphenol is any one of catechin, anthocyanin and quercetin.

5. An emulsion according to claim 1, wherein said material which is insoluble or having low solubility with respect to water and oil comprises at least one of androstenedione and taxol.

6. An emulsion according to claim 1, wherein said material which is insoluble or having low solubility with respect to water and oil is validamycin.

7. An emulsion according to claim 1, wherein said emulsifying agent is a polyglycerol fatty acid ester.

8. An emulsion according to claim 7, wherein said polyglycerol fatty acid ester is selected from the group consisting of tetraglycerol monoester, hexaglycerol monoester and polyglycerol oleic acid ester.

9. An emulsion according to claim 1, wherein said oil is vegetable oil.

10. An emulsion according to claim 9, wherein a main component of said vegetable oil is triglyceride.

11. An emulsion according to claim 1, wherein said alcohol is selected from the group consisting of methanol, hydrous methanol, ethanol, hydrous ethanol, propanol, hydrous propanol, butanol and hydrous butanol.

12. An emulsion according to claim 8, wherein said polyglycerol fatty acid ester comprises polyglycerol oleic acid ester.

13. An emulsion according to claim 2, wherein said material which is insoluble or having low solubility with respect to water and oil comprises polyphenol.

14. An emulsion according to claim 2, wherein said material which is insoluble or having low solubility with respect to water and oil comprises at least one of androstenedione and taxol.

15. An emulsion according to claim 2, wherein said emulsifying agent is a polyglycerol fatty acid ester.

16. An emulsion according to claim 15, wherein said polyglycerol fatty acid ester is selected from the group consisting of tetraglycerol monoester, hexaglycerol monoester and polyglycerol oleic acid ester.

17. An emulsion according to claim 2, wherein said oil is vegetable oil.

18. An emulsion according to claim 2, wherein said alcohol is selected from the group consisting of methanol, hydrous methanol, ethanol, hydrous ethanol, propanol, hydrous propanol, butanol and hydrous butanol.

19. An emulsion according to claim 1, wherein said material which is insoluble or having low solubility with respect to water and oil is dissolved into said alcohol at a concentration of 20–30 wt % with respect to said alcohol.

20. An emulsion according to claim 2, wherein said material which is insoluble or having low solubility with respect to water and oil is dissolved into said alcohol at a concentration of 20–30 wt % with respect to said alcohol.

* * * * *

UNITED STATES PATENT AND TRADEMARK OFFICE
CERTIFICATE OF CORRECTION

PATENT NO. : 6,538,019 B1
DATED : March 25, 2003
INVENTOR(S) : Mitsutoshi Nakajima et al.

It is certified that error appears in the above-identified patent and that said Letters Patent is hereby corrected as shown below:

Title page,
Item [56], References Cited, FOREIGN PATENT DOCUMENTS, on the line listing reference "WO-973078" change "JP" to -- WIPO -- and change "WO-973078" to -- WO-9730783 --; insert the following reference cited by the examiner:
-- JP    61-209035   A  *   9/1986 --.
Item [57], ABSTRACT,
Line 1, change "According to the present invention, it is possible to produce" to -- Functional --;
Line 2, change "are" to -- is --;
Line 3, change "have" to -- has --;
Line 4, delete "so as to obtain emulsions which";
Line 12, before "vegetable" insert -- the --.

Column 1,
Line 31, change "polyphenol" to -- polyphenols --.
Line 38, change "a extremely" to -- an extremely --.
Line 45, after "material" insert -- which is --; change "solublility" to -- solubility --.
Lines 48 and 57, change "is" to -- are --;
Line 52, change "is" to -- are --; after "provided" insert -- according to the invention --.

Column 2,
Line 9, after "Any" insert -- appropriate --.
Line 24, delete "to".
Line 40, change "the triolein" to -- a triolein --; change "purity 90%" to -- purity of 90% --.

Signed and Sealed this

Twenty-sixth Day of August, 2003

JAMES E. ROGAN
*Director of the United States Patent and Trademark Office*